(12) United States Patent
Chen et al.

(10) Patent No.: US 9,045,733 B2
(45) Date of Patent: Jun. 2, 2015

(54) ULTRASOUND ENHANCED GROWTH OF MICROORGANISMS

(75) Inventors: Jie Chen, Edmonton (CA); James Xing, Edmonton (CA); Woon T. Ang, Edmonton (CA)

(73) Assignee: Intelligentnano Inc., Edmonton, Alberta (CA)

( * ) Notice: Subject to any disclaimer, the term of this patent is extended or adjusted under 35 U.S.C. 154(b) by 218 days.

(21) Appl. No.: 13/060,860

(22) PCT Filed: Aug. 26, 2009

(86) PCT No.: PCT/CA2009/001189
§ 371 (c)(1),
(2), (4) Date: Apr. 20, 2011

(87) PCT Pub. No.: WO2010/022509
PCT Pub. Date: Mar. 4, 2010

(65) Prior Publication Data
US 2011/0189748 A1    Aug. 4, 2011

Related U.S. Application Data

(60) Provisional application No. 61/091,830, filed on Aug. 26, 2008.

(51) Int. Cl.
| | | |
|---|---|---|
| C12N 13/00 | (2006.01) | |
| C12P 1/00 | (2006.01) | |
| C12N 5/0789 | (2010.01) | |
| C12M 1/42 | (2006.01) | |

(52) U.S. Cl.
CPC .............. C12N 5/0647 (2013.01); C12N 13/00 (2013.01); *C12M 35/04* (2013.01)

(58) Field of Classification Search
USPC .......................................... 424/41, 71.1, 171
See application file for complete search history.

(56) References Cited

U.S. PATENT DOCUMENTS

| | | | |
|---|---|---|---|
| 4,530,360 A | 7/1985 | Duarte | |
| 4,879,011 A | 11/1989 | Schram | |
| 5,554,384 A | 9/1996 | Samuels et al. | |
| 6,835,560 B2 | 12/2004 | Greene | |
| 8,079,966 B2 | 12/2011 | El-Bialy et al. | |
| 8,292,834 B2 | 10/2012 | El-Bialy et al. | |
| 9,005,942 B2 | 4/2015 | Chen et al. | |
| 9,012,192 B2 | 4/2015 | Chen et al. | |
| 2003/0153077 A1* | 8/2003 | Pitt et al. | 435/383 |
| 2004/0191906 A1 | 9/2004 | Holzer | |
| 2004/0197908 A1 | 10/2004 | Ueda et al. | |
| 2006/0106424 A1 | 5/2006 | Bachem | |
| 2007/0020757 A1 | 1/2007 | Zhang et al. | |
| 2007/0082397 A1 | 4/2007 | Hasson et al. | |
| 2007/0249046 A1 | 10/2007 | Shields, Jr. | |
| 2007/0299539 A1* | 12/2007 | Othman et al. | 623/23.72 |
| 2008/0021327 A1 | 1/2008 | El-Bialy et al. | |
| 2010/0034735 A1 | 2/2010 | Chen et al. | |
| 2011/0189748 A1 | 8/2011 | Chen et al. | |
| 2011/0275054 A1 | 11/2011 | Chen et al. | |
| 2012/0059287 A1 | 3/2012 | El-Bialy et al. | |
| 2012/0100525 A1 | 4/2012 | Chen et al. | |
| 2012/0135392 A1 | 5/2012 | El-Bialy et al. | |
| 2013/0022957 A1 | 1/2013 | Chen et al. | |
| 2013/0265856 A1 | 10/2013 | Choi et al. | |

FOREIGN PATENT DOCUMENTS

| | | |
|---|---|---|
| CN | 200980138627.0 | 3/2012 |
| CN | 200980138267.0 | 2/2013 |
| CN | 200980138627.0 | 2/2013 |
| CN | 200980138627.0 | 3/2013 |
| CN | 200980138627.0 | 8/2013 |
| CN | 200980138627.0 | 11/2013 |
| CN | 200980138627.0 | 9/2014 |
| CN | 200980138627.0 | 3/2015 |
| EP | 1566201 | 8/2005 |
| EP | 09 809 150.7 | 11/2011 |
| EP | 09 809 150.7 | 2/2012 |
| EP | 09809149.9 | 2/2012 |
| EP | 09809149.9 | 3/2013 |
| EP | 09 809 150.7 | 7/2013 |
| EP | 09809149.9 | 6/2014 |
| EP | 09 809 150.7 | 7/2014 |
| EP | 09809149.9 | 11/2014 |
| WO | 03/089581 | 10/2003 |
| WO | 2008/004752 | 1/2008 |
| WO | 2010/022508 | 3/2010 |
| WO | 2010/022509 | 3/2010 |
| WO | PCT/CA2009/001188 | 3/2011 |
| WO | PCT/CA2009/001189 | 3/2011 |
| WO | PCT/CA2012/000873 | 1/2013 |

(Continued)

OTHER PUBLICATIONS

Yusuf, Chisti "Sonobioreactors: Using Ultrasound for Enhanced Microbial productivity" Institute of Technology and Engineering, PN456, Massey University, Private Bag 11 222, Palmesrston North, New Zealand.

(Continued)

*Primary Examiner* — Ruth Davis
(74) *Attorney, Agent, or Firm* — Evan Law Group LLC

(57) ABSTRACT

A method of increasing the rate of growth, useful product production, or protein expression of a microorganism includes the step of exposing the microorganism to ultrasound having a frequency greater than about 1 MHz.

13 Claims, 4 Drawing Sheets

(56) References Cited

FOREIGN PATENT DOCUMENTS

| WO | 2013/040688 | 3/2013 |
|---|---|---|
| WO | PCT/CA2012/000873 | 2/2014 |

OTHER PUBLICATIONS

Sontag, Werner et al. "Expression of Heat Shock Proteins After Ultrasound Exposure In HL-60 Cells", Ultrasound in Med. & Biol. vol. 35, No. 6, pp. 1032-1041, 2009.

Parvizi, J. et al.; Low-Intensity Ultrasound Stimulates Proteoglycan Synthesis in Rat Chondrocytes by Increasing Aggrecan Gene Expression; Journal of Orthopaedic Research; 1999; vol. 17; pp. 488-494.

Lin, L et al.; Ultrasound-Induced Pysiological Effects and Secondary Metabolite (Saponin) Production in Panax Ginseng Cell Cultures; Ultrasound in Med. & Biol.; 2001; vol. 27, No. 8; pp. 1147-1152.

Yoon, J.H. et al.; Introducing Pulsed Low-Intensity Ultrasound to Culturing Human Umbilical Cord-Derived Mesenchymal Stem Cells; Biotechnol Letter; 2009; vol. 3; pp. 329-335.

Xie, C.-g. et al., "Marrow mesenchymal stem cells transduced with TPO/FL genes as support for ex vivo expansion of hematopoietic stem/progenitor cells", Cellular and Molecular Life Sciences, vol. 62, pp. 2495-2507, (2005).

Xing, J.Z. et al., "Ultrasound-enhanced monoclonal antibody production", Ultrasound in Medicine and Biology, vol. 38, No. 11, pp. 1949-1957, (2012).

Wofsy, D. et al., "Successful treatment of autoimmunity in NZB/NZW $F_1$ mice with monoclonal antibody to L3T4", Journal of Experimental Medicine, vol. 161, pp. 378-391, (1985).

Yi, H. et al., "Depleting anti-CD4 monoclonal antibody (GK1.5) treatment: influence on regulatory CD4+CD25+Foxp3+ T cells in mice", Transplantation, vol. 85, No. 8, pp. 1167-1174, (2008).

Markvicheva, E. et al., "The effect of low-intensity ultrasound on hybridoma cell proliferation and monoclonal antibody production in hollow fiber bioreactor", European Journal of Cell Biology, vol. 69, No. suppl. 42, #465, p. 155, Conference Abstract from the $21^{st}$ Annual Meeting of the German Society for Cell Biology, Hamburg, Germany, Mar. 24-28, 1996.

Lv, Y. et al., "Effects of low-intensity pulsed ultrasound on cell viability, proliferation and neural differentiation of induced pluripotent stem cells-derived neural crest stem cells", Biotechnology Letters, vol. 35, issue 12, pp. 2201-2212, (2013).

International Search Report dated Dec. 10, 2009, for PCT application No. PCT/CA2009/001188, 11 pages.

Bensinger, W. et al., "Improving stem cell mobilization strategies: future directions", Bone Marrow Transplantation, vol. 43, pp. 181-195, (2009).

Birch, J.R. et al., "Antibody production", Advanced Drug Delivery Reviews, vol. 58, pp. 671-685, (2006).

Bordignon, C. "Stem-cell therapies for blood diseases", Nature, vol. 441, pp. 1100-1102, (2006).

Brada, S. et al., "The supportive effects of erythropoietin and mast cell growth factor on CD34+/CD36-sorted bone marrow cells of myelodysplasia patients", Blood, vol. 88, pp. 505-510, (1996).

Brada, S.J.L. et al., "Characterization of the erythropoiesis in myelodysplasia by means of ferrokinetic studies, in vitro erythroid colony formation and soluble transferrin receptor", Leukemia, vol. 12, pp. 340-345, (1998).

Bradley, M.B. et al., "Cord blood immunology and stem cell transplantation", Human Immunology, vol. 66, pp. 431-446, (2005).

Brugger, W. et al., "Reconstitution of hematopoiesis after high-dose chemotherapy by autologous progenitor cells generated ex vivo", The New England Journal of Medicine, vol. 333, No. 5, pp. 283-287, (1995).

Choi, W.H. et al., "Low-intensity ultrasound increased colony forming unit-fibroblasts of mesenchymal stem cells during primary culture", Tissue Engineering: Part C, vol. 17, No. 5, pp. 517-526, (2011).

Conneally, E. et al., "Expansion in vitro of transplantable human cord blood stem cells demonstrated using a quantitative assay of their lympho-myeloid repopulating activity in nonobese diabetic-scid/scid mice", Proceedings of the National Academy of Sciences of the United States of America, vol. 94, pp. 9836-9841, (1997).

Copelan, E.A. "Hematopoietic stem-cell transplantation", The New England Journal of Medicine, vol. 354, No. 17, pp. 1813-1826, (2006).

Dahlberg, a. et al., "Ex vivo expansion of human hematopoietic stem and progenitor cells", Blood, vol. 117, No. 23, pp. 6083-6090, (2011).

El-Bialy, T. "Therapeutic ultrasound applications in craniofacial growth, healing and tissue engineering", Rejuvenation Research, vol. 10, No. 3, pp. 367-371, (2007).

Gluckman, E. "Ten years of cord blood transplantation: from bench to bedside", British Journal of Haematology, vol. 147, pp. 192-199, (2009).

Guilak, F. et al., "Control of stem cell fate by physical interactions with the extracellular matrix", Cell Stem Cell, vol. 5, pp. 17-26, (2009).

Gul, H. et al., "Valproic acid increases CXCR4 expression in hematopoietic stem/progenitor cells by chromatin remodeling", Stem Cells and Development, vol. 18, No. 6, pp. 831-838, (2009).

Gul, H. et al., "Magnetic carbon nanotube labelling for haematopoietic stem/progenitor cell tracking", Nanotechnology, vol. 21, pp. 1-9, (2010).

Harris, G.R., "Progress in medical ultrasound expositmetry", IEEE Transactions on Ultrasonics, Ferroelectrics, and Frequency Control, vol. 52, No. 5, pp. 717-736, (2005).

Heckman, J.D. et al., "Acceleration of tibial fracture-healing by non-invasive, low-intensity pulsed ultrasound", The Journal of Bone & Joint Surgery, vol. 76-A, No. 1, pp. 26-34, (1994).

Iwashina, T. et al., "Low-intensity pulsed ultrasound stimulates cell proliferation and proteoglycan production in rabbit intervertebral disc cells cultured in alginate", Biomaterials, vol. 27, pp. 354-361, (2006).

Kaufmann, H. et al., "Metabolic engineering of mammalian cells for higher protein yield", Gene Transfer and Expression in Mammalian Cells, Chapter 15, pp. 457-469, (2003).

Kaushansky, K. "Thrombopoietin and the hematopoietic stem cell", Blood, vol. 92, No. 1, pp. 1-3, (1998).

McNiece, I. et al., "Ex vivo expanded peripheral blood progenitor cells provide rapid neutrophil recovery after high-dose chemotherapy in patients with breast cancer", Blood, vol. 96, No. 9, pp. 3001-3007, (2000).

Mottram, P.L. et al., "Transgenic anti-CD4 monoclonal antibody secretion by mouse segmental pancreas allografts promotes long term survival", Transplant Immunology, vol. 8, pp. 203-209, (2000).

Petzer, A.L. et al., "Differential cytokine effects on primitive (CD34+ CD38−) human hematopoietic cells: novel responses to Flt3-ligand and thrombopoietin", The Journal of Experimental Medicine, vol. 183, pp. 2551-2558, (1996).

Praloran, V. et al.,"Blood erythroid progenitors (CFU-E and BFU-E) in acute lymphoblastic leukemias", Blut, vol. 58, pp. 75-78, (1989).

Qiu, Y. et al., "The correlation between acoustic cavitation and sonoporation involved in ultrasound-mediated DNA transfection with polyethylenimine (PEI) in vitro", Journal of Controlled Release, vol. 145, pp. 40-48, (2010).

Rodrigues, M.E. et al., "Technological progresses in monoclonal antibody production systems", Biotechnology Progress, vol. 26, No. 2, pp. 332-351, (2010).

Rubinstein, P. "Why cord blood?", Human Immunology, vol. 67, pp. 398-404, (2006).

Scheven, B.A.A. et al., "Therapeutic ultrasound for dental tissue repair", Medical Hypotheses, vol. 73, pp. 591-593, (2009).

Shah, A.J. et al., "Flt3 ligand induces proliferation of quiescent human bone marrow $CD34^+CD38-$ cells and maintains progenitor cells in vitro", Blood, vol. 87, No. 9, pp. 3563-3570, (1996).

Sriram, S. et al., "In vivo immunomodulation by monoclonal anti-CD4 antibody II. Effect on T cell response to myelin basic protein and experimental allergic encephalomyelitis", The Journal of Immunology, vol. 141, No. 2, pp. 464-468, (1988).

Doherty, T.A. et al., "CD4+ cells are required for chronic eosinophilic lung inflammation but not airway remodeling", American Journal of Physiology—Lung Cellular and Molecular Physiology, vol. 296, pp. L229-L235, (2009).

(56) References Cited

OTHER PUBLICATIONS

Villaron, E.M. et al., "In leukapheresis products from non-Hodgkin's lymphoma patients, the immature hematopoietic progenitors show higher CD90 and CD34 antigenic expression", Transfusion and Apheresis Science, vol. 37, pp. 145-156, (2007).
Wurm, F.M. "Production of recombinant protein therapeutics in cultivated mammalian cells", Nature Biotechnology, vol. 22, No. 11, pp. 1393-1398, (2004).
Zhang, Z-J. et al., "The effects of pulsed low-intensity ultrasound on chondrocyte viability, proliferation, gene expression and matrix production", Ultrasound in Medicine & Biology, vol. 29, No. 11, pp. 1645-1651, (2003).
Ziskin, M.C., "Applications of ultrasound in medicine—comparison with other modalities", Ultrasound: Medical Applications, Biological Effects, and Hazard Potential, pp. 49-59, (1987).
International Search Report and Written Opinion dated Jan. 11, 2013, for PCT application No. PCT/CA2012/000873, 14 pages.
Regueira, T.B. et al., "Molecular basis for mycophenolic acid biosynthesis in penicillium brevicompactum", Applied and Environmental Microbiology, vol. 77, No. 9, pp. 3035-3043, (2011).
Gul-Uludag, H. et al., "Abstract of Ultrasound stimulation enhances proliferation of hemtopoietic stem/progenitor cells: Implications for clinical transplantation, gene and cellular therapies", Annual Conference of International Society for Cellular Therapy, Philadelphia, PA, May 25, Cytotherapt, 2:40, (2010).
Parvizi, J. et al., "Low-intensity ultrasound stimulates proteoglycan synthesis in rat chondrocytes by increasing aggrecan gene expression", Journal of Orthopaedic Research, vol. 17, No. 4, pp. 488-494, (1999).
Lin, L. et al., "Ultrasound-induced physiological effects and secondary metabolite (saponin) production in panax ginseng cell cultures", Ultrasound in Med. & Biology, vol. 27, No. 8, pp. 1147-1152, (2001).
Yoon, J.H. et al., "Introducing pulsed low-intensity ultrasound to culturing human umbilical cord-derived mesenchymal stem cells", Biotechnol Letter, vol. 31, pp. 329-335, (2009).
Chisti, Y. "Sonobioreactors: using ultrasound for enhanced microbial productivity", Trends in Biotechnology, vol. 21, No. 2, pp. 89-93, (2003).
Sontag, W. et al., "Expression of heat shock proteins after ultrasound exposure in HL-60 cells", Ultrasound in Med. & Biol., vol. 35, No. 6, pp. 1032-1041, (2009).
Ang, W.T. et al., "Design and implementation of therapeutic ultrasound generating circuit for dental tissue formation and tooth-root healing", IEEE Transactions on Biomedical Circuits and Systems, vol. 4, No. 1, pp. 49-61, (2010).
Bradner, J.R. et al., "Qualitative assessment of hydrolytic activities in antarctic microfungi grown at different temperatures on solid media", World Journal of Microbiology & Biotechnology, vol. 15, pp. 131-132, (1999).
Chen, H. et al., "Key technologies for bioethanol production from lignocelluloses", Biotechnology Advances, vol. 28, No. 5, pp. 556-562, (2010).
Doan, N. et al., "In vitro effects of therapeutic ultrasound on cell proliferation, protein synthesis, and cytokine production by human fibroblasts, osteoblasts, and monocytes", J. Oral Maxillofac Surg., vol. 57, pp. 409-419, (1999).
Khanal, S.K. et al., "Ultrasound enhanced glucose release from corn in ethanol plants", Biotechnology and Bioengineering, vol. 98, No. 5, pp. 978-985, (2007).
Kobayashi, Y. et al., "Low-intensity pulsed ultrasound stimulates cell proliferation, proteoglycan synthesis and expression of growth factor-related genes in human nucleus pulposus cell line", European Cells and Materials, vol. 17, pp. 15-22, (2009).
Leung, K-S. et al., "Complex tibial fracture outcomes following treatment with low-intensity pulsed ultrasound", Ultrasound in Med. & Biology, vol. 30, No. 3, pp. 389-395, (2004).
Min, B-H. et al., "Effects of low-intensity ultrasound (LIUS) stimulation on human cartilage explants", Scand J. Rheumatol., vol. 35, pp. 305-311, (2006).
Osawa, K. et al., "Osteoinduction by microbubble-enhanced transcutaneous sonoporation of human bone morphogenetic protein-2", The Journal of Gene Medicine, vol. 11, pp. 633-641, (2009).
Singhania R.R. et al., "Plant-Based biofuels—An introduction", A. "Handbook of Plant-Based Biofuels", CRC Press, pp. 3-12, (2009).
Rubin, C. et al., "The use of low intensity ultrasound to accelerate the healing of fractures", J. Bone Joint Surg. Am., vol. 83, pp. 259-270, (2001).
Soetaert, W. et al., "Biofuels in Perspective", Biofuels, pp. 1-7, John Wiley & Sons Ltd, (2009).
Sun, J-S. et al., "In vitro effects of low-intensity ultrasound stimulation on the bone cells", Journal of Biomedical Materials Research, vol. 57, pp. 449-456, (2001).
Nikolic, S. et al., "Ultrasound-assisted production of bioethanol by simultaneous saccharification and fermentation of corn meal", Food Chemistry, vol. 122, pp. 216-222, (2010).
Teather, R.M. et al., "Use of Congo red-polysaccharide interactions in enumeration and characterization of cellulolytic bacteria from the bovine rumen", Applied and Environmental Microbiology, vol. 43, No. 4, pp. 777-780, (1982).
Wood, B.E. et al., "Ultrasound stimulates ethanol production during the simultaneous saccharification and fermentation of mixed waste office paper", Biotechnol Progress, vol. 13, No. 3, pp. 232-237, (1997).
Yang, F. et al., "Enhancement of enzymatic in situ saccharification of cellulose in aqueous-ionic liquid media by ultrasonic intensification", Carbohydrate Polymers, vol. 81, No. 2, pp. 311-316, (2010).
Zhou, S. et al., "Molecular mechanism of low intensity pulsed ultrasound in human skin fibroblast", J. Biol. Chem., vol. 279, pp. 54463-54469, (2004).
Shaheen, M. et al., "Application of low-intensity pulsed ultrasound to increase bio-ethanol production", Renewable Energy, vol. 57, pp. 462-468, (2013).
Zhao, Y. et al., "Applications of ultrasound to enhance mycophenolic acid production" Ultrasound in Medicine & Biology, vol. 38, issue 9, pp. 1582-1588, (2012).
Radel, S. et al., "Viability of yeast cells in well controlled propagating and standing ultrasonic plane waves", Ultrasonics, vol. 38, pp. 633-637, (2000).
Sainz Herran, N. et al., "Influence of ultrasound amplitude and duty cycle on fungal morphology and broth rheology of aspergillus terreus", World J. Microbiol Biotechnol, vol. 26, pp. 1409-1418, (2010).
Saif Ur Rehman, M. et al., "Use of ultrasound in the production of bioethanol from lignocellulosic biomass", Energy Education Science and Technology Part A: Energy Science and Research, vol. 30, issue 2, pp. 1391-1410, (2013).
Ohgren, K., et al., "High temperature enzymatic prehydrolysis prior to simultaneous saccharification and fermentation of steam pretreated corn stover for ethanol production", Enzyme and Microbial Technology, vol. 40, pp. 607-613, 2007).
Gamauf. C. et al., "Characterization of the bga1-encoded glycoside hydrolase family 35 β-galactosidase of hypocrea jecorina with glacto-β-D-galactanase activity", The FEBS Journal, vol. 274, pp. 1691-1700, (2007).
Xu, P. et al., "Low-intensity pulsed ultrasound-mediated stimulation of hematopoietic stem/progenitor cell viability, proliferation and differentiation in vitro", Biotechnology Letters, vol. 34, issue 10, pp. 1965-1973, (2012).
International Search Report dated Dec. 9, 2009 for PCT application No. PCT/CA2009/001189, 11 pages.
El-Bialy, T. et al., "Cell expansion genes expression by therapeutic ultrasound. Pros and cons", Canadian Accoustics, vol. 36, No. 3, pp. 40-41, (2008).
Ang, W. T. et al., "System-on-chip ultrasonic transducer for dental tissue formation and stem cell growth and differentiation", Proceedings of the IEEE Symposium on Circuits and Systems, Seattle, pp. 1818-1821, (May 2008).
Brian997, "Stem cells", found at http://hronrad.wordpress.com/2013/12/05/stem-cells/, pp. 1-3, May 12, 2013.
U.S. Appl. No. 13/060,851, Jan. 14, 2014, pp. 3.
U.S. Appl. No. 13/238,947, Jan. 14, 2014, pp. 3.
U.S. Appl. No. 13/060,860, Mar. 13, 2013. pp. 16.
U.S. Appl. No. 13/060,860, Aug. 20, 2013, pp. 13.

(56) References Cited

OTHER PUBLICATIONS

U.S. Appl. No. 13/060,860, Nov. 13, 2013, pp. 8.
U.S. Appl. No. 13/238,978, May 16, 2013, pp. 5.
U.S. Appl. No. 13/238,978, Jul. 17, 2013, pp. 19.
U.S. Appl. No. 13/238,978, Jan. 17, 2014, pp. 6.
U.S. Appl. No. 13/238,947, Apr. 17, 2013, pp. 7.
U.S. Appl. No. 13/238, 947, Sep. 17, 2013, pp. 31.
U.S. Appl. No. 13/060,851, Apr. 17, 2013, pp. 7.
U.S. Appl. No. 13/060,851, Sep. 10, 2013, pp. 20.
U.S. Appl. No. 13/060,860, Dec. 28, 2012, pp. 7.
U.S. Appl. No. 13/238,978, filed Sep. 21, 2011.
U.S. Appl. No. 13/060,851, filed Aug. 26, 2009.
U.S. Appl. No. 13/238,947, filed Sep. 21, 2011.
U.S. Appl. No. 13/060,851, Jun. 2, 2014, pp. 28.
U.S. Appl. No. 13/238,947, Jun. 11, 2014, pp. 25.
Takagi, M. "Cell processing engineering for ex-vivo expansion of hematopoietic cells", Journal of Bioscience and Bioengineering, vol. 99, No. 3, pp. 189-196, (2005).
Barnett, S.B. et al., "Is pulsed ultrasound mutagenic?", Ultrasound Med. Biol., Supplemental 2, pp. 45-48, (1983).
Pui, P.W.S. et al., "Batch and semicontinuous aggregation and sedimentation of hybridoma cells by acoustic resonance fields", Biotechnology Prog., vol. 11, No. 2, pp. 146-152, (1995).
U.S. Appl. No. 13/060,851, Dec. 4, 2014, pp. 13.
U.S. Appl. No. 13/238,978, Dec. 18, 2014, pp. 20.

\* cited by examiner (a) The plate made of ultrasound transducer array (b) The liquid within the bottom on top of the plate will receive even ultrasound treatment

ULTRASOUND ENHANCED GROWTH OF MICROORGANISMS

CROSS REFERENCE TO RELATED APPLICATIONS

This application claims the priority benefit of U.S. Provisional Application No. 61/091,830 filed on Aug. 26, 2008 entitled "METHOD TO INCREASE THE RATE OF PROTEIN EXPRESSION IN CELL", the contents of which are incorporated herein by reference, where permitted.

FIELD OF THE INVENTION

The present method relates to methods of increasing protein expression in microorganisms. In particular, the present invention relates to methods of increasing protein expression of microorganisms by exposing the cells to ultrasonic stimulation.

BACKGROUND OF THE INVENTION

Cell cultures are used widely in science and industry for purposes varying from protein production, food and beverage fermentation to pharmaceutical production. Cell cultures are often used in laboratory settings for research and disease diagnosis and, with the advent of genetic engineering, modified organisms are more and more commonly used for the production of medical proteins, antibiotics, insulin, hormones, and other biomedically-important molecules.

Fermentation is one of the most important processes in the pharmaceutical industry. Industrial fermentation loosely refers to the breakdown of organic substances and re-assembly into other substances. Fermenter culture in industrial capacity often refers to highly oxygenated and aerobic growth conditions. For instance, penicillin, which brought enormous profits and public expectations, was produced industrially using a deep fermentation process. When a particular organism is introduced into a selected growth medium, the medium is inoculated with the particular organism. Growth of the inoculums does not occur immediately, but follows a lag phase. Subsequently, the rate of growth of the organism steadily increases, for a certain period—this period is the log or exponential phase. After the exponential phase, the rate of growth slows down, due to the continuously falling concentrations of nutrients and the continuously increasing (accumulating) concentrations of toxic substances. This phase, where the increase of the rate of growth is checked, is the deceleration phase. After the deceleration phase, growth ceases and the culture enters a stationary phase or steady state.

The fermentation industry relies on bacterial and fungal cultures to produce alcoholic beverages, process a wide variety of foods, transform corn and other raw materials into biofuels, neutralize toxic spills in a process commonly known as "bioremediation," breakdown liquid and solid wastes, and, as previously mentioned, create a plethora of biologically-significant compounds.

In almost all useful applications of cell cultures, the rate at which the desired product is produced is limited only by the rate at which protein expression occurs, and the growth rate of the cells used in production. Industrial fermentation most often takes place in a specially designed environment in which cells are grown in suspension. The fermenter maximizes cell growth by carefully maintaining optimal temperature and agitating the contained mixture to ensure transfer of nutrients into and metabolic byproducts out of the cell. However, it is difficult to ensure that the turbulence in the tank is pervasive enough to affect the cells on the microscopic level; there is often a relatively stagnant region directly adjacent to the walls of the cells and the fermenter itself. This naturally has a negative effect on the nutrient and toxin transfer to and from the cells, and reduces the rate of protein expression, which lowers the overall productivity of the fermentation process.

As fermentation is a widely practiced art and has many industrial applications, it is clear that some method of improving the rate of cell protein expression would be desirable.

Ultrasonic stimulation creates "microcavitation", or the creation of minute bubbles in a liquid known as "microcavities." With each sound wave, these bubbles expand and contract, creating tremendous force and turbulence on a microscopic scale. In some cases, this sound wave is powerful enough to collapse the cavities, which causes even more extreme turbulence, high temperatures, and free radicals in the vicinity of the former cavity. These collapses are powerful enough to dislodge or even destroy cells.

Ultrasonic applications rely on these processes—one common use of ultrasound is as an effective cleaning agent; if the intensity is high enough, collapse cavitation is the dominant factor in the cells' environment. This can strip harmful bacteria off of a surface, and even kill a large number of them. The effectiveness of this technique has been proven by applying ultrasound to one end of a glass tube, using frequencies around 100 kHz and intensities around 40 W/cm$^2$—it was found that approximately 88% of the bacteria were removed from the surface of the tube. Similar experiments have been carried out in a variety of situations, including stripping biofilms off of reverse osmosis membranes. Ultrasound is now actively sold to laboratories as a cleaning aid.

As well as dislodging bacteria, very high intensity ultrasound (>10 W/cm$^2$) has been used to kill suspended bacteria—this relies on collapse cavitation to rend the bacteria's membrane.

Applications also exist for lower-intensity ultrasound; it is believed that ultrasonic waves can improve the rate of bone growth and indeed, almost 80% of North American physiotherapists possess ultrasonic emitters for the purpose of encouraging speedy recovery. A recent study has indicated that only low-intensity ultrasound is effective in this situation, and low-intensity pulsed ultrasound (LIPUS) devices are currently being marketed for this purpose. One method has been revealed in U.S. Pat. No. 4,530,360 to Duarte (1982).

A method of using low-intensity pulsed ultrasound to aid the healing of flesh wounds is shown in U.S. Pat. Application 2006/0106424 A1 by Bachem (2005). The method utilizes ultrasound to increase the phagocytotic action of the human body's macrophages. However, the method provides no solution for the use of ultrasound outside the confines of a wound.

U.S. Patent Application No. US 2003/0153077 A1 details a method in which low-intensity ultrasound can stimulate the growth of biofilms and other cells—by balancing the beneficial turbulence produced by collapse cavitation with its accompanying negative effects, it was found that low-intensity ultrasound can improve growth rates of cells by up to 50%. The experimenters tested their findings on human and bacterial cells, using frequencies from about 20 kHz to about 1 MHz and intensities encompassing the range from 1 to 5000 mW/cm$^2$. Unfortunately, though increased cell growth is beneficial to the fermentation process, the parameters investigated by this group do not provide the optimal rate of protein expression in fermentation processes.

SUMMARY OF THE INVENTION

The present invention provides a method of increasing the rate of cell growth or protein expression, or both, in prokaryotic cells by stimulating them with calibrated ultrasound. The enhanced cell growth or protein expression may take place in the context of a useful process, such as fermentation anaerobic digestion or bioremediation, for example.

In one aspect, the invention comprises a method of enhancing the rate of cell growth or protein expression in a cell culture, or both, through exposure to ultrasound of specified frequencies and intensities. These methods are beneficial to cells in the vast majority of environments, creating turbulence on the microscopic scale in the area immediately adjacent to the walls of the cells and other solid surfaces.

The ultrasound may have a frequency between about 1 MHz and about 10 MHz, and preferably between about 1 MHz and 2 MHz, depending inter alia on the species of cell used in culture. In one embodiment, the ultrasound has a frequency between about 1.4 MHz to about 1.6 MHz. In one embodiment, it consists of a pulsed ultrasound, which assists in minimizing temperature increase of the environment. In one embodiment, pulses generated at a duty cycle of approximately 4:1 (off:on), with a pulse period of approximately 1 second, are effective. In one embodiment, the ultrasound is calibrated to achieve a balance of the harmful effects of "collapse cavitations" caused by the ultrasound and the beneficial turbulence it affords the cells, allowing increased nutrient uptake and metabolic byproduct expulsion.

In one aspect of the invention, there is also a method of sensing the intensity of the ultrasonic waves employed, as "felt" by the target cells. This is not, however, necessary in all circumstances, and the method can proceed without such detection. The measurement can be taken with any ultrasound-measuring device operatively connected to the ultrasound emitter. In one embodiment, the method further comprises the step of relaying collected information back to the ultrasonic emitter if said sensor is employed. This may be through a wired or wireless connection.

In another aspect, the invention comprises a method of correcting the emitted output to maximize the effectiveness of the ultrasound, based on the sensed intensities, if said sensor is employed. This assists in maximizing protein expression.

The target cells may be eukaryotic or prokaryotic, and may comprise fungal or bacterial cells. The cells may be natural or modified.

The ultrasound may possess an intensity greater than about 10 $mW/cm^2$ up to about 5000 $mW/cm^2$, depending on the fragility of the cells in culture.

In one embodiment, the ultrasound can be directed such that reflections and interference are minimized, or tuned to give maximum effectiveness to the ultrasonic emission.

In one embodiment, the ultrasonic emitter may be placed inside a fermenter, or attached to a solid emitting surface outside a fermenter, or other suitable configurations.

In situations of fermentation that do not occur in a fermenter or digestion, the method may still be applied, the ultrasound emitted to have maximum coverage of the cells whose protein expression is desired to be enhanced. In such cases, for example, in situ bacterial bioremediation, ultrasound emitters may be strategically placed, and may be moved periodically.

BRIEF DESCRIPTIONS OF THE DRAWINGS

In order that the above-recited and other features and advantages of the present invention will be readily understood, a more particular description of the invention is given. A specific example thereof is detailed, the result of which are illustrated in the appended figures. The following example is only a single embodiment of the invention, and is not to be considered in any way the limit of its scope. In the accompanying figures:

FIG. 1 is a schematic depiction of one embodiment of the invention described herein, allowing greater yield of useful biomaterials in an industrial setting. Ultrasound is applied by a piezoelectric transducer to a cell culture in a conventional fermentation tank. The transducer may be positioned to ensure maximum and uniform distribution of the ultrasound throughout the growth medium FIG. 2 shows microscopic images of a fungi (*T. reesei*) which has been stimulated with ultrasound and a control. The number of fungi is significantly increased after applying ultrasound. Identification number 844 was assigned to strand Rut C-30—(a) control after three days under 25× enlarged microscopic magnitude; (b) after three days under 25× enlarged (c) control after three days under 50× enlargement; and (d) ultrasound after three days under 50× enlargement.

FIG. 3 is a comparison of the cellulase activity of *T. reesei* (strain Rut-C30 or 844) with ultrasound and without ultrasound treatment (844 Control, or 844 CK) after three days. Here 844 A2, 844 C2 and 844 E2 stand for different LIPUS intensities: 10 $mW/cm^2$, 50 $mW/cm^2$ and 100 $mW/cm^2$, respectively. This illustrates the effectiveness of LIPUS, as well as its reliance on specific properties of the ultrasound, such as intensity and frequency. It can be seen that ultrasound of too high an intensity can actually hinder growth.

FIG. 4 shows biomass comparison after ultrasound treatment (mg) of different intensities. CK-2 is the control. A1-3 is 80 $mW/cm^2$, D1-3 is 60 $mW/cm^2$ and E1-3 is 30 $mW/cm^2$.

DETAILED DESCRIPTION OF EMBODIMENTS OF THE INVENTION

Figure 1:
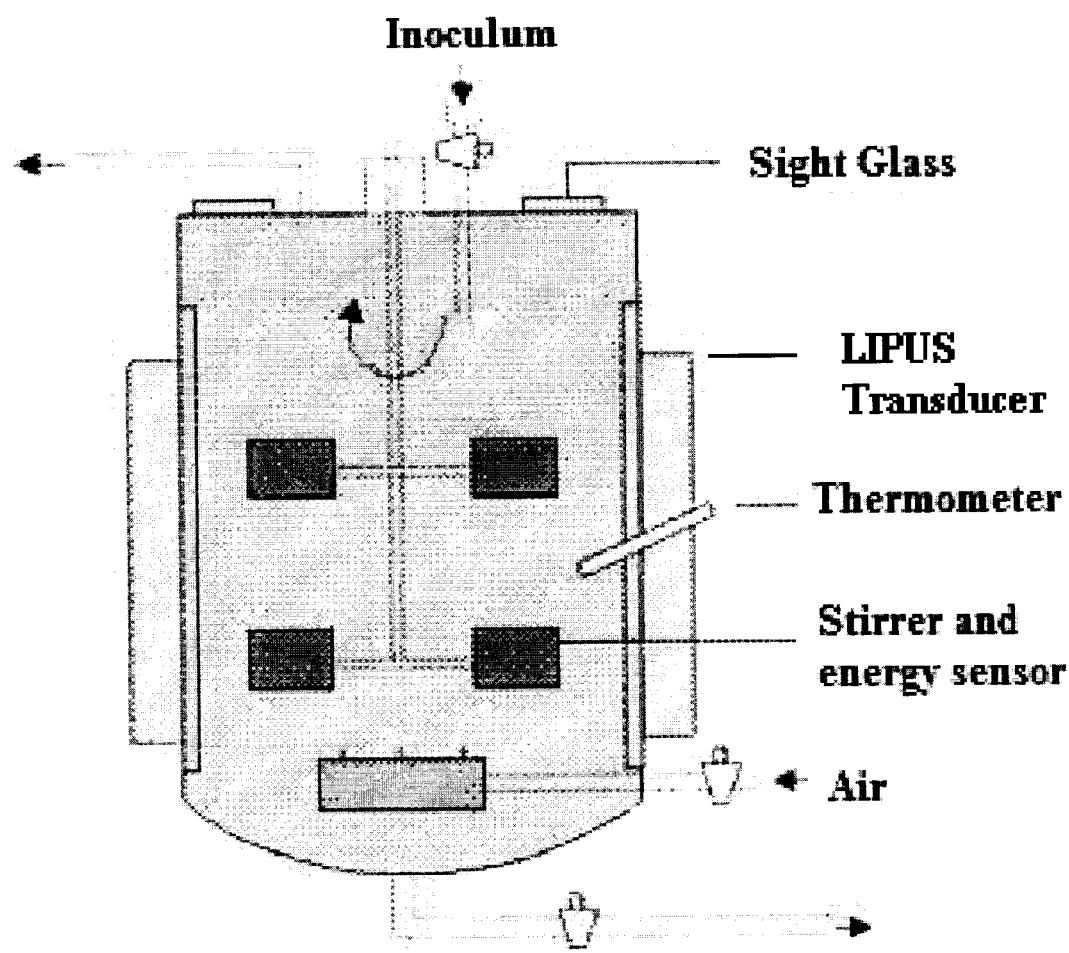

Embodiments of the invention may be understood by referring to the following description and drawings. The methods of the present invention, as generally described herein, can be practiced and varied in many ways. Thus, the following more detailed description of the methods of the present invention is not intended to limit the scope of the invention, as claimed. Instead, the detailed description is merely representative of the presently considered embodiments.

The term "microorganism" includes prokarotic organisms and unicellular eukaryotic organisms. Microorganisms may include, without limitation, bacteria, fungi, archaea, and protists. Microorganisms include unicellular organisms which may be used in industrially useful processes, such as fermentation, bioremediation or production of bioproducts.

As used herein, the term "fermentation" is broadly used to mean the bulk growth of microorganisms on or in some growth medium. No distinction is made between aerobic and anaerobic metabolism when the word is used in this sense. Anaerobic fermentation is the energy-yielding anaerobic metabolic breakdown of a nutrient molecule, such as glucose, without net oxidation. Fermentation may typically yield lactate, acetic acid, ethanol, or some other simple product.

The present invention comprises the application of high-frequency ultrasound to microorganisms to enhance their growth or to enhance production of proteins or other molecules or compounds produced by the microorganisms. The subject microorganisms may exist in liquid or solid culture, or may exist in uncontrolled environments. The useful products produced by microorganisms subjected to a method of the present invention may include gases, oils, organic acids, alcohols or proteins. In one embodiment, the microorganisms may be involved in breaking down or digesting a substrate, such as in an anaerobic digester or a bioremediation process.

It is not known with certainty why ultrasound applied in accordance with the present invention enhances cell growth or protein production. Without being limited to any one theory, it appears that the present invention increases cell growth or protein expression by allowing more rapid transport of essential materials into the cell, and allowing quicker dispersion of metabolic by-products away from the cell.

Though most fermentation tanks already address this problem by stirring or shaking the cell cultures inside of them, it is theorized that a microscopic buffer remains around solid surfaces or cell walls in which fluid movement is greatly constrained. If the fluid immersing the cell is stagnant in the area directly adjacent to the cell, it is not conducive to the transport of small molecules—such as oxygen, amino acids, carbon dioxide or other gases—away from or towards the cell.

A liquid surrounding a cell culture contains bubbles of gas which compress and relax, causing them to contract and expand, when exposed to ultrasound. This movement creates resultant forces on the liquid surrounding the gas bubbles—when the bubble is compressed, liquid is "pulled" into the area around the now-smaller bubble, and when the bubble expands, liquid is pushed away. This causes considerable turbulence on the microscopic level. This turbulence is even slightly topical, as gas bubbles will preferentially form near cell walls or solid surfaces, precisely the original locations of the stagnancy.

If the pressures are high enough (this is caused by ultrasound of a high intensity), bubbles can collapse down to nothing. Simple thermodynamics will demonstrate that the temperature will rise precipitously in such an incidence—one study claims temperatures as high as 5000 K—and the collapse results in a shock wave of heat and "shear force," or force directed towards the bubble's center. The collapse produces turbulence on a massive scale, allowing even faster transfer of nutrients and wastes—but at the same time, the heat and force may be intense enough to damage or tear open the cell wall itself. The intensity and frequency of ultrasound in this invention must be able to afford a balance between the harmful and beneficial effects of the cavitations.

The present invention is intended to aid cell growth or protein expression by increasing the transfer of substances in the vicinity of the cellular membranes. Enhanced cell growth and protein expression are usually positively co-related, and enhancement of one will typically result in, or be caused by, enhancement of the other.

*T. reesei* is the fungus variety that is used in the creation of almost all biofuels, including conventional ethanol, butanol, and cellulosic ethanol. The latter product is an efficient and relatively inexpensive biofuel that can be made from organic waste and other inedible plant matter. Cellulosic ethanol especially is hailed as the future alternative to fossil fuels, and the commercialization of its production is already beginning. One major hurdle to this commercialization, however, is the almost prohibitive cost and the immense time involved in its production. Optimizing *T. reesei* will allow butanol producers to increase the rate at which the *T. reesei* cells undergo protein expression—and thus, increase the output of butanol.

Cellulosic ethanol is produced from the non-food portions of crops, such as straw and other organic wastes. Though this is greatly preferred to using edible materials to produce fuels, it again is a more costly and time-intensive process, and embodiments of the present invention could increase the rate at which cellulosic ethanol can be produced.

High frequency ultrasound (greater than about 1 MHz) may be applied in many different contexts to enhance cell growth or protein expression in a cell culture. Such potential applications include increased protein expression in laboratory cultures, allowing faster tests and diagnoses, faster production of pharmaceuticals, growth hormones, regulatory factors, proteins, and a wide array of other biomedical substances.

The biocultures of yeasts, bacteria, fungi, and other such microorganisms that transform chemical substances represents another possible implementation of the technology, including implementations not specifically mentioned above.

We have found that ultrasound has beneficial effects on cell growth in microbial cell culture when applied at a high frequency, greater than about 1 MHz. Prior art use of ultrasound stimulation involved frequencies in the range of 20 kHz to 1 MHz. We have surprisingly found that that the optimal frequency in many cases was higher than 1 MHz. Thus, in one embodiment, the ultrasound frequency is greater than about 1 MHz, and less than about 2 MHz. Around 1.5 MHz, tests revealed that many cell types, including stem cells and other animal cells, were allowed maximum "micro-agitation" while only sustaining minimal damages to cellular structure. Therefore, in one embodiment, the ultrasound is greater than about 1.4 MHz, and less than about 1.6 MHz. In one preferred embodiment, 1.4 MHz and about 1.6 MHz were found to be particularly useful when applied to *T. reesei*.

Possible applications also exist for employing the technology in non-cultured examples; that is, cells that are not in specifically controlled environments. Though such environments were the locations of microbial cell culture in a laboratory setting, embodiments of the present invention may also be applied in a less controlled situation, such as bioremediation in the environment, or large scale anaerobic digesters.

Different cells have different strengths and weaknesses, and all cells may not require the same frequencies and intensities. These differences are predicted to be greatest between the classes of microorganisms, prokaryotes and eukaryotes. The method herein provides the windows of frequencies and intensities that allow for optimal performance among these difference varieties of cells.

The intensity of the ultrasound energy may be greater than about 5 $mW/cm^2$ up to about 5000 $mW/cm^2$. In one embodiment, the intensity is preferably between about 40 $mW/cm^2$ and about 80 $mW/cm^2$, and in one embodiment, an optimal intensity was about 60 $mW/cm^2$.

In one embodiment, the cells in question are subjected to ultrasonic stimulation from an ultrasonic emitter placed near enough to the target area to deliver waves of a specific frequency and intensity, which will be discussed below. In one embodiment, the ultrasound is applied during logarithmic growth phase of a cell culture; however, its beneficial effects may be realized during any growth phase. Sustained stimulation with ultrasound is not necessary, increased growth rate or protein expression may be obtained by applying ultrasound in intervals less than one hour per 24 hour period. In one embodiment, stimulation intervals of only between about 10 minutes and 20 minutes per 24 hour period is all that is required to reap benefits of ultrasound application.

Optimization of a suitable frequency and intensity for any given microbe and growth condition may be determined by empirical study, without undue experimentation, by those skilled in the art. In general, however, prokaryotic cells are naturally more durable than eukaryotic cells and thus can withstand a higher intensity ultrasonic stimulation. Intensity ranges have been briefly discussed in the patent application of Pitt et al, entitled "METHOD TO INCREASE THE RATE OF CELL GROWTH" (Pub. No. US 2003/0153077 A1). The conclusions reached therein place the approximate intensity ranges for eukaryotic cells at 8-50 mW/cm$^2$ and for prokaryotic cells at 2-2.2 W/cm$^2$. All trials conducted in the Pitt et al. patent used a frequency of 70 kHz.

In one embodiment, the ultrasound is pulsed, as prolonged exposure can cause heat buildup and damage the treated cells. The duration and timing of the pulses may again be chosen by one skilled in the art by empirical study. In one embodiment, a duty cycle of 1:4 and a 1 s cycle was utilized in our trials (that is, 200 μs of activity followed by 800 μs of 'silence') The on/off ratio and cycle duration may be varied as required or desired. Other duty cycles may be suitable, depending inter alia on the species of cell, the frequency and intensity of the ultrasound.

When several features of the present invention are combined, the resulting application may be termed "LIPUS", which refers to low-intensity pulsed ultrasound.

In one embodiment, the invention comprises the use of an ultrasound sensor, operatively connected to the ultrasound transmitter, permitting a feedback loop control over frequency and intensity. The intensity measurement can be taken with any suitable ultrasound-measuring device, which are commercially available. In one embodiment, the method further comprises the step of relaying collected information back to the ultrasonic emitter if said sensor is employed. This may be through a wired or wireless connection. A schematic representation of such a setup employing a feedback sensor is shown in FIG. 1B. The feedback loop is used to maintain the ultrasound frequency and intensity at a pre-determined level or range.

Figure 6:
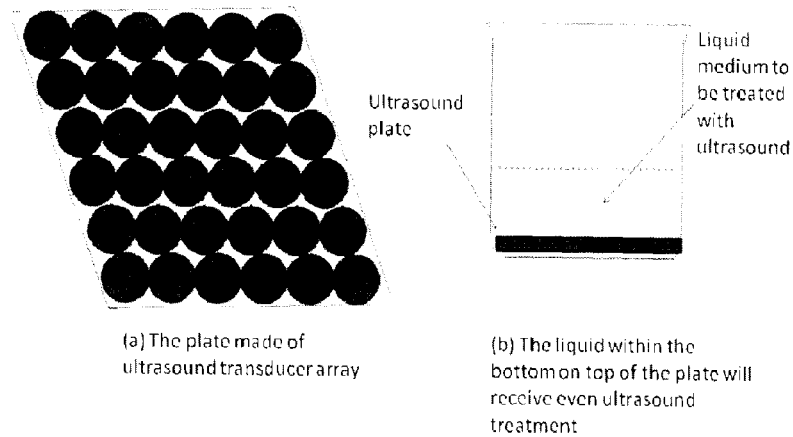
FIG. 6 shows one embodiment of an ultrasound transducer array for use in larger volume liquid culture.
Figure 7:
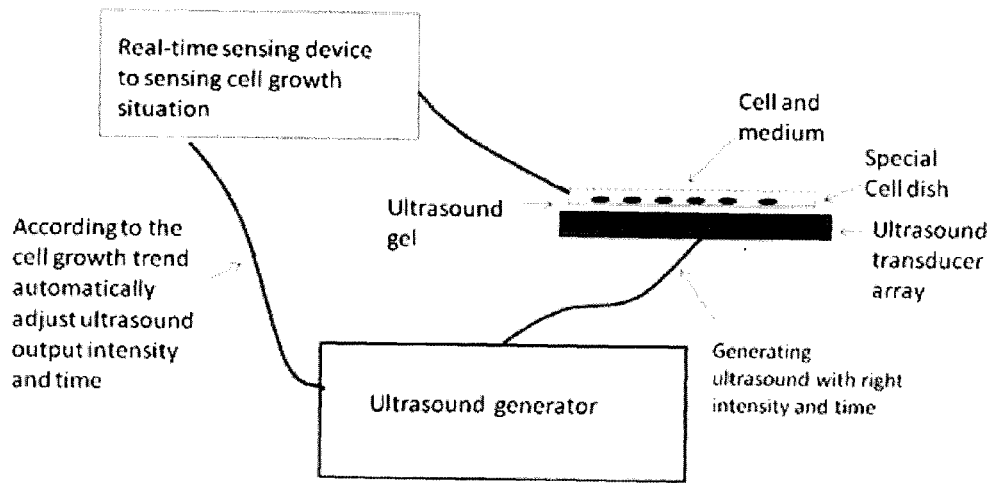
FIG. 7 is a schematic representation of an ultrasound system employing system feedback.

As mentioned above, these methods are suitable for use with cells grown in controlled and many non-controlled environments, including those in suspension. In one embodiment, where larger volumes of liquid cell culture are subjected to ultrasound, the ultrasound may be applied with a transducer array, to provide a more uniform application of ultrasound energy. As may be seen in FIG. 6, an ultrasound plate comprising a plurality of individual transducers may be disposed within a cell culture vessel. In one embodiment, the array may be disposed at the bottom of the vessel. With consistent agitation, the cell culture will be exposed to a relatively uniform amount of ultrasound energy during any application period. FIG. 6 illustrates a 5 L beaker, however, the concept may be extended fermentation tanks of significantly larger volume, such as that illustrated in FIG. 1. The design that the ultrasound emitted from the ultrasound plate generates an even amount of ultrasound across the array so that liquid in the beaker will be treated more evenly than with a single transducer at a given location.

The present invention may be embodied in other specific forms without departing from its structures, methods, or other essential characteristics as broadly described herein and claimed hereafter. The described embodiments are to be considered in all respects only as is, therefore, indicated by the appended claims, rather than by the foregoing description. All changes that come within the meaning and equivalence of the claims are to be embraced within their scope.

The following examples are meant to be merely exemplary and not in any way limit the claimed invention.

EXAMPLES

The following examples are intended to illustrate the claimed invention and not to restrict the claimed invention in any manner.

Example 1

Growth of *Penicillium brevicompactum*

One vial of cryopreserved *P. brevicompactum* spores was diluted 1/20 with sterile water. 1 ml of the spore suspension was dispensed into 500 ml flask containing 75 ml of PDA agar and incubated for 9 days at room temperature. 50 ml sterile 0.01% Tween80 was added to the spore culture flask and the spores were scraped into solution. The solution was transferred to a sterile container. 200 μL of the spore suspension was inoculated into a 125 ml plastic flask with 25 ml seed medium. The seed flasks were incubated at 27° C., 200 rpm (2" throw) for 48 hours. 0.5 ml of seed culture was inoculated into flasks containing 25 ml production medium and incubated Incubate the production flasks at 27° C., 200 rpm (2" throw). 10 minutes of ultrasound treatment were applied to the each flask everyday with different intensities.

|  | Seed Medium Amount (g/L) | Production Medium Amount (g/L) |
| --- | --- | --- |
| Sucrose | 52.0 | 150.0 |
| Glycine | 7.5 | 14 |
| Yeast extract | 2.0 | 0 |
| MgSO4 7H2O | 1.0 | 1.0 |
| KH2PO4 | 1.0 | 1.0 |
| JEC TE solution | 1.0 ml | 1.0 ml |

* JEC TE solution containing NaMoO4•2H2O, H3BO3, CuSO4•5H2O, FeSO4•7H2O, MnSO4•H2O, ZnSO4•7H2O and Citric Acid After 4 days incubation, culture were collected and sent for MPA quantification by using Agilent system. Extraction of MPA from the fermentation broth was carried out by adding one volume of 50% acetonitrile in water, followed by shaking at 200 rpm for 1 hour at room temperature. The extraction was centrifuged at 8000 rpm for 30 minutes. The resulting supernatant was filtrated through 0.22 μm filter and was analyzed by HPLC for MPA concentration.

Figure 4:
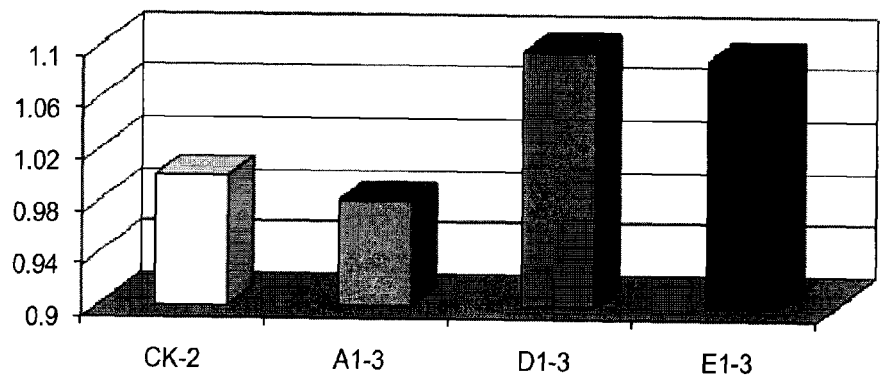

Biomass analysis were carried out according to standard filter paper/oven method. Culture treated with ultrasound at D (60 mW/cm$^2$) and E (30 mW/cm$^2$) levels gave a elevated 10% and 9% biomass production respectively, as is shown in FIG. 4.

Example 2

MPA Quantitation by HPLC

Calibration and quality control standards were prepared by dilution of MPA stock solution with acetonitrile. Calibration standards containing 0.5, 1.0, 10, 50, 100, 250, 500 μg/ml MPA were used to construct calibration curve using 1/x2 linear regression.

HPLC was performed on an Agilent 1100 HPLC system. The analytical column was SymmetryShield RP-8 (100×4.6 mm, 3.5 μm) with a guard column (SymmetryShield 20×3.9 mm, 5 μm). Mobile phase A was 35:65% (v/v) MeOH: 5 mM NaH2PO4 (pH 4.0) and mobile phase B was 90:10% (v/v)

MeOH: 2.5 mM NaH2PO4 (pH 4.0). Elution of MPA from the column was carried out with a linear gradient mobile phase at a flow rate of 1.0 ml/min from 0 to 80% B in 8 min, from 80% to 100% B in 4 min, 100% B kept for 4 min, from 100% B to 0% B in 1 min, and 0% B kept for 5 min. MPA absorbance was monitored at 215 nm wavelength.

Figure 5:
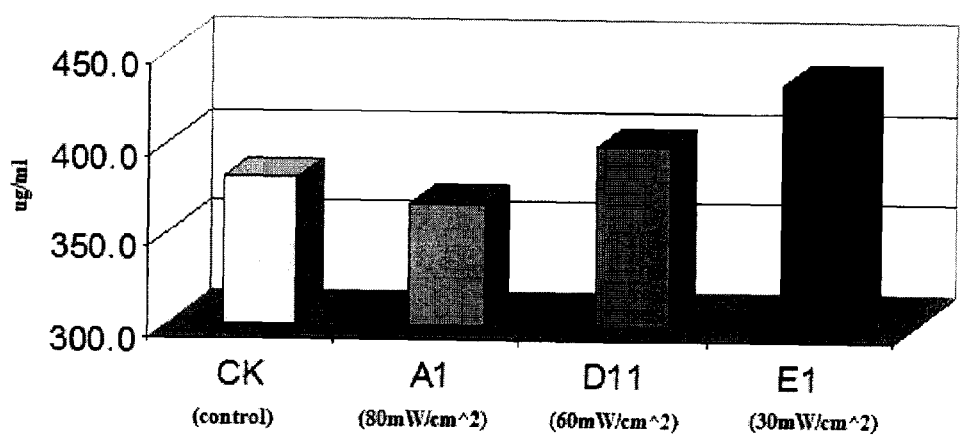
FIG. 5 shows the concentration (μg/ml) of a fermentation product (mycophenolic acid) after ultrasound treatment of different intensities (same as shown in FIG. 4) compared to a control.

MPA concentration from culture treated with ultrasound at D and E levels shown 6-14% increase in MPA production, as seen in FIG. 5.

Example 3

Higher Intensity Ultrasound

Certain higher level of ultrasound treatment might suppress the microorganism growth. As may be seen in FIGS. 4 and 5, *P. brevicompactum* treated with 80 mW/cm$^2$ showed a slight decrease in biomass and MPA production under the specific growth conditions used, whereas ultrasound at 30 and 60 mW/cm$^2$ showed increases in biomass and MPA production.

Example 4

Growth of *Trichoderma reesei*

Figure 2:
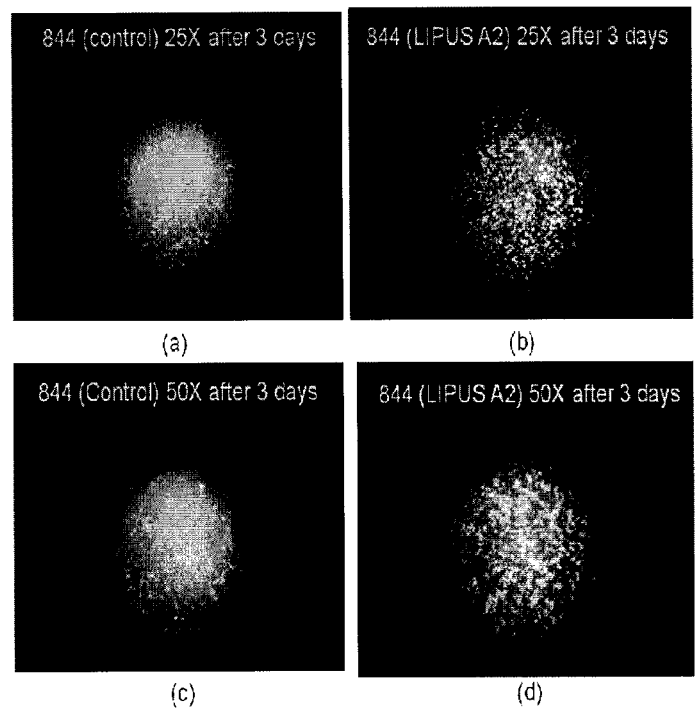
Figure 3:
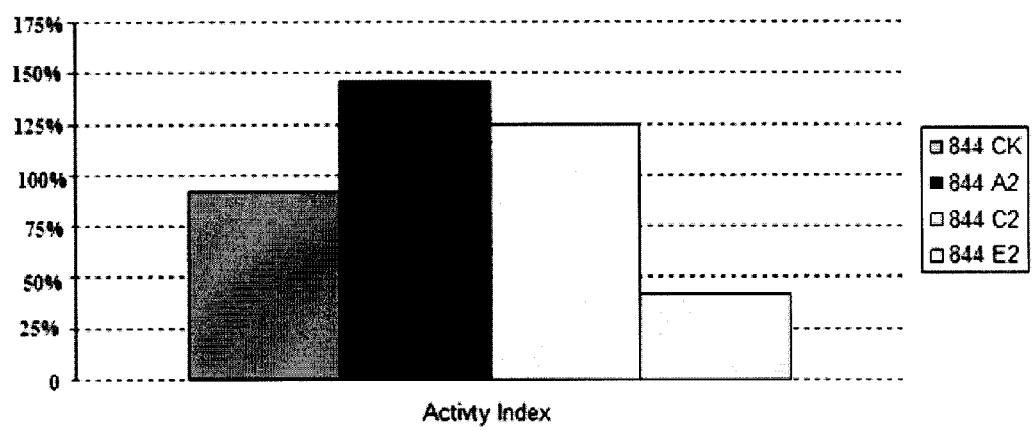

The following two *Trichoderma reesei* strains were used #843-ALK01120=QM9414; #844-ALK02374=Rut C-30 (Roal Oy, 2007). The CMT method was applied for growth under 12 hrs/12 hrs light/dark conditions. A 1 mm diameter plug of fungi is taken from the original plate and inoculated on the centre of 60 mm Petri dish, previously treated with Carboxymethyl Cellulose (CMC) agar containing 1% Congo red. The plates were kept at room temperature for 2 hrs to allow the agar to solidify. Ten minutes of LIPUS treatment was applied on the fungi at 2 hrs, 4 hrs, 21 hrs, 24 hrs, 48 hrs, and 72 hrs. after the initial inoculation at different intensities: 20 mW/cm$^2$ for 844 A2, 50 mW/cm$^2$ for 844 C2, and 100 mW/cm$^2$ for 844 E2. Plates were then de-stained by 1 M sodium chloride (NaCl), and the relative cellulase activity was measured using the ICMC index procedure (Teather and Wood, 1982; Bradner et al, 1999) and microscopic observation. As shown in FIG. 2, LIPUS at 20 and 40 mW/cm$^2$ indeed stimulated culture growth compared to the control with no LIPUS treatment (844 CK), but higher intensities could also inhibit growth; thus, optimizing the LIPUS intensity is preferred.

What is claimed:

1. A method of increasing the rate of growth, useful product production, or protein expression of a microorganism, comprising:
    exposing the microorganism to ultrasound having a frequency from greater than about 1 MHz to about 10 MHz, wherein the microorganism comprises a fungus.
2. The method of claim 1 wherein the ultrasound is pulsed.
3. The method of claim 2, wherein the frequency of the ultrasound is from greater than about 1 MHz to 2 MHz.
4. The method of claim 3, wherein the frequency of the ultrasound is between about 1.4 MHz and about 1.6 MHz.
5. The method of claim 4 wherein the frequency of the ultrasound is about 1.5 MHz.
6. The method of claim 1, wherein the intensity of the ultrasound is from about 20 mW/cm$^2$ to about 100 mW/cm$^2$.
7. The method of claim 1 wherein the fungus comprises a *Penicillium* species or a *Trichoderma* species.
8. The method of claim 1 wherein the ultrasound is applied in periodic intervals.
9. The method of claim 8 wherein the ultrasound is applied in one or more intervals totaling less than 60 minutes in a 24 hour period.
10. The method of claim 9 wherein the ultrasound is applied in a single interval of 10 or 20 minutes in a 24 hour period.
11. The method of claim 1, wherein the ultrasound is pulsed, the frequency of the ultrasound is between about 1.4 MHz and about 1.6 MHz, and the ultrasound is applied in periodic intervals.
12. The method of claim 1, wherein the fungus comprises *Penicillium brevicompactum*.
13. The method of claim 1, wherein the fungus comprises *Trichoderma reesei*.

* * * * *